United States Patent [19]

Sirkar

[11] 4,380,678
[45] Apr. 19, 1983

[54] MULTI-STAGE ALDOSES TO POLYOLS PROCESS

[75] Inventor: Amalesh K. Sirkar, Lawrenceville, N.J.

[73] Assignee: Hydrocarbon Research, Inc., Lawrenceville, N.J.

[21] Appl. No.: 226,998

[22] Filed: Mar. 20, 1981

[51] Int. Cl.³ ............... C07C 31/18; C07C 31/20; C07C 31/22; C07C 31/26
[52] U.S. Cl. .................................................. 568/863
[58] Field of Search ............................. 568/861, 863

[56] References Cited

U.S. PATENT DOCUMENTS

| | | | |
|---|---|---|---|
| 2,004,135 | 6/1935 | Rothrock | 568/861 |
| 2,174,651 | 10/1939 | Byrkit | 568/863 |
| 2,456,633 | 12/1948 | Haensel | 252/460 |
| 2,549,416 | 4/1951 | Brooks | 568/881 |
| 2,851,390 | 12/1957 | Gwynn et al. | 568/882 |
| 2,852,570 | 9/1958 | Conradin et al. | 568/861 |
| 2,965,679 | 12/1960 | Conradin et al. | 568/861 |
| 3,481,836 | 12/1969 | Nomura et al. | 568/863 |
| 3,676,364 | 7/1972 | Coates | 568/861 |

FOREIGN PATENT DOCUMENTS

| | | | |
|---|---|---|---|
| 523789 | 4/1956 | Canada | 568/863 |
| 35860 | 1/1965 | German Democratic Rep. | 568/863 |
| 688515 | 3/1953 | United Kingdom | 568/863 |

OTHER PUBLICATIONS

Lange, "Handbook of Chemistry", 10th ed., (1961), pp. 951, 952.

Primary Examiner—Joseph E. Evans
Attorney, Agent, or Firm—V. A. Mallare; F. A. Wilson

[57] ABSTRACT

Aldoses such as glucose solution are catalytically hydrogenated in a multiple-stage fixed-bed reaction process to produce glycerol and other polyol products. The feedstream pH to each reactor is controlled to between about 7 and 14 by adding an alkaline promotor material such as calcium hydroxide. First-stage reaction zone conditions are 130°–180° C. temperature, 500–2000 psig hydrogen partial pressure, and feedstream liquid space velocity is within range of 0.5–3.5 $V_f/Hr/V_c$. The first reactor uses a high activity nickel catalyst to produce at least about 98 W % conversion to alditol such as sorbitol solution.

The resulting alditols such as 15–40 W % sorbitol solution in water is catalytically hydrocracked in a second-stage fixed-bed reaction zone preferably using a high-activity nickel catalyst to produce at least about 30 W % conversion to glycerol and glycols products. Second-stage reaction zone conditions are 420°–520° F. temperature, 1200–2000 psig hydrogen partial pressure, and liquid hourly space velocity of 1.5 to 3.0. The reaction products are separated in a recovery step, and unconverted heavy alditol feed can be diluted and recycled to the second-stage reaction zone for further hydrogenolysis to produce 40–90 W % glycerol product. Sorbitol conversion is maintained preferably at between about 30–70 W % and a purge stream containing unconverted sugars is passed to a third-stage catalytic reaction zone for further conversion to alditols and polyols.

10 Claims, 1 Drawing Figure

MULTI-STAGE ALDOSES TO POLYOLS PROCESS

BACKGROUND OF INVENTION

1. Field of Invention

This invention pertains to the catalytic hydrogenation of aldoses such as glucose to produce glycerol and other polyols. It pertains more particularly to a multiple-stage process wherein a portion of the sugars produced from the second or alditol (sorbitol) hydrogenolysis stage is passed to a third hydrogenation stage for further conversion to glycerol.

2. Description of Prior Art

It has been noted that the catalytic hydrogenolysis of alditols such as sorbitol in a fixed bed reactor using nickel catalyst to produce polyols such as glycerol and glycols also forms some polyglycerols and aldoses (glucose) from the feed of alditols (sorbitol), respectively. Dehydrogenation of alcohols to sugars and dehydration of glycerol to polyglycerols presents the problem of build up of such substances in the recovery step because of the usual recycle stream to the sorbitol cracking reaction zone, which not only contains unconverted sorbitol and alditols but also the sugars and polyglycerols which are neither removed in the distillation step nor extracted out by the solvent in an extraction step, if used. To prevent such buildup of sugars and polyglycerols which is detrimental to process operations, withdrawal of a purge stream has been used from the distillation separation step. However, such a purge stream presents a loss of valuable products and reactants along with the sugars from the process, thereby decreasing yields and increasing costs. Thus, it is desirable to recover the sugars, polyglycerols and unconverted sorbitol by some appropriate reprocessing steps.

A disclosure regarding hydrogenolysis of sorbitol is provided by Clark in Industrial & Engineering Chemistry, Vol. 50, No. 8 (Aug. 1958), page 1125. Aqueous solution containing 40% of 99% D-sorbitol were used with 1% calcium hydroxide promotor and 50% nickel on kieselguhr catalyst suspended in a slurry with the feed in a stirred reactor. Conditions used were 2000–5600 psi hydrogen partial pressure, 215°–245° C. (419°–473° F.) temperature and reaction times up to 400 minutes (6.7 hrs) to produce glycerol, ethylene glycol, propylene glycol, and other more minor products.

U.S. Pat. No. 2,965,679 to Conradin discloses a similar process for producing glycerol and glycols from sugar alcohols using a suspended nickel on kieselguhr catalyst in an autoclave type reactor. Reaction conditions are 200°–300° C. temperature, 500–1000 atmospheres pressure and pH of 8–10, followed by filtration to remove catalyst and separation of the products.

Van Ling et al disclosed in Journal of Applied Chemisty, Vol 19, pages 43–45, hydrogenation experiments using slurried catalyst in autoclave reactor on feeds of sucrose, glucose and fructose in methanol-water solution to produce glycerol. Catalyst used was $CuO\text{-}CeO_2\text{-}SiO_2$ with 0–5% $Ca(OH)_2$ addition to the feed. Reaction conditions used were 200°–250° C. temperature, 100–300 atmospheres pressure and 10–120 minutes reaction time.

U.S. Pat. No. 3,471,580 to Hellwig et al discloses that by using a single or multi-stage upflow ebullated bed catalytic reactor at 200°–550° F. temperature and 700–3500 psia hydrogen partial pressure, glycerol and glycols can be produced from saccharides. Examples of the conditions used for converting a sorbitol type feed to glycerol in a single stage reaction were about 375° F. temperature, 1700 psia hydrogen partial pressure, 1.2 liquid hourly space velocity (LHSV), and using nickel on alumina catalyst to produce roughly 50 W % glycerol and 20 W % ethylene glycol and propylene glycol, with the remainder being methanol, ethanol, isopropanol, and other products (col. 5, lines 40–53).

It is believed that none of these known processes are presently being used commercially to produce glycerol and related products on a continuous basis. Thus, further process improvements in conversion of aldoses and alditols are desired not only for achieving continuous operations, reduced reaction conditions and increased glycerol product yields, particularly using improved catalysts in fixed-bed reactors, but to prevent loss of valuable sugars and glycols which are usually removed from the distillation step by a purge stream.

SUMMARY OF INVENTION

The present invention discloses an improved, multiple-stage catalytic reaction process for hydrogenation of aldoses such as glucose, mannose, and sucrose to produce alditols and polyols such as glycerol and other polyol products. In the second or alditol hydrogenolysis reaction step, some additional materials such as unconverted sorbitol, $C_4$–$C_5$ alditols, $C_4$–$C_6$ sugars, and polyglycerols are produced. These compounds are high boiling viscous materials which tend to decompose when exposed to high temperatures. In the process of separating these compounds from other polyols, these compounds are obtained as a mixture and at different temperature levels depending on the separation arrangement used, which can be either vacuum distillation or a combination of extraction and distillation.

To avoid decomposition of the unconverted aldose and alditol compounds and for easy recycling of these materials to the catalytic reaction steps for further conversion, it has been found that water, with or without some low boiling alcohols such as ethanol or methanol, can be advantageously injected into the viscous mixture to be recycled to the reaction steps. The purpose of such water injection is to quench the mixture to below the decomposition temperatures of the viscous compounds in the mixture, and also allow the material to be pumped rather easily by diluting it with a low viscosity solvent material. Furthermore, to avoid decomposition of the compounds in the mixture to be recycled, the heat requirement for heating the feed up to the reaction temperature may be supplied by preheating the hydrogen stream and/or by injecting high pressure steam into the reactor.

As a further process improvement, to prevent loss of $C_4$ to $C_6$ sugars and polyglycerols from the second or alditol hydrogenolysis step caused by their usual withdrawal in a purge stream following product distillation steps, it has been found particularly advantageous to further react the purge stream material containing such sugars in a third hydrogenation reaction step, usually at more severe conditions than for the first and second stage reaction steps. In such third reaction step, the remaining sugars are further catalytically hydrogenated to produce alditols and alcohols in presence of a catalyst such as nickel supported on silica-alumina. It is expected that the other aldose materials present will also be converted to alditols in presence of the same catalyst. By such additional catalytic reaction step, whatever sugars remain after the second stage or sorbitol cracking reactor are converted back to alcohols, and thus any significant loss of reactant and product from the process is avoided.

It should be noted that in addition to formation of sugars in the second stage sorbitol hydrogenolysis reactor, some amount of polyglycerol (produced by dehydration and polymerization reactions) and other compounds similar to polyglycerol may be produced in the sorbitol cracking reactor. Formation of these compounds is expected to increase as the temperature of reaction increases above about 400° F. Thus, passing the usual purge stream to a third reaction step also prevents buildup of polyglycerols, if this compound does not crack at a rate faster than it is being produced in the second stage reactor. Although it is desirable to control concentration of undesired sugars in the polyols products by adjusting the sorbitol catalytic cracking reaction conditions such that polyglycerol does not build up in the system, it is usually necessary to withdraw a purge stream from the distillation step to prevent build up of polyglycerols and to increase the yield of glycerol product. Thus, passing this purge stream to a third reactor at more severe conditions increases the yield of useful products from the process.

DESCRIPTION OF PREFERRED EMBODIMENTS

Figure 1:
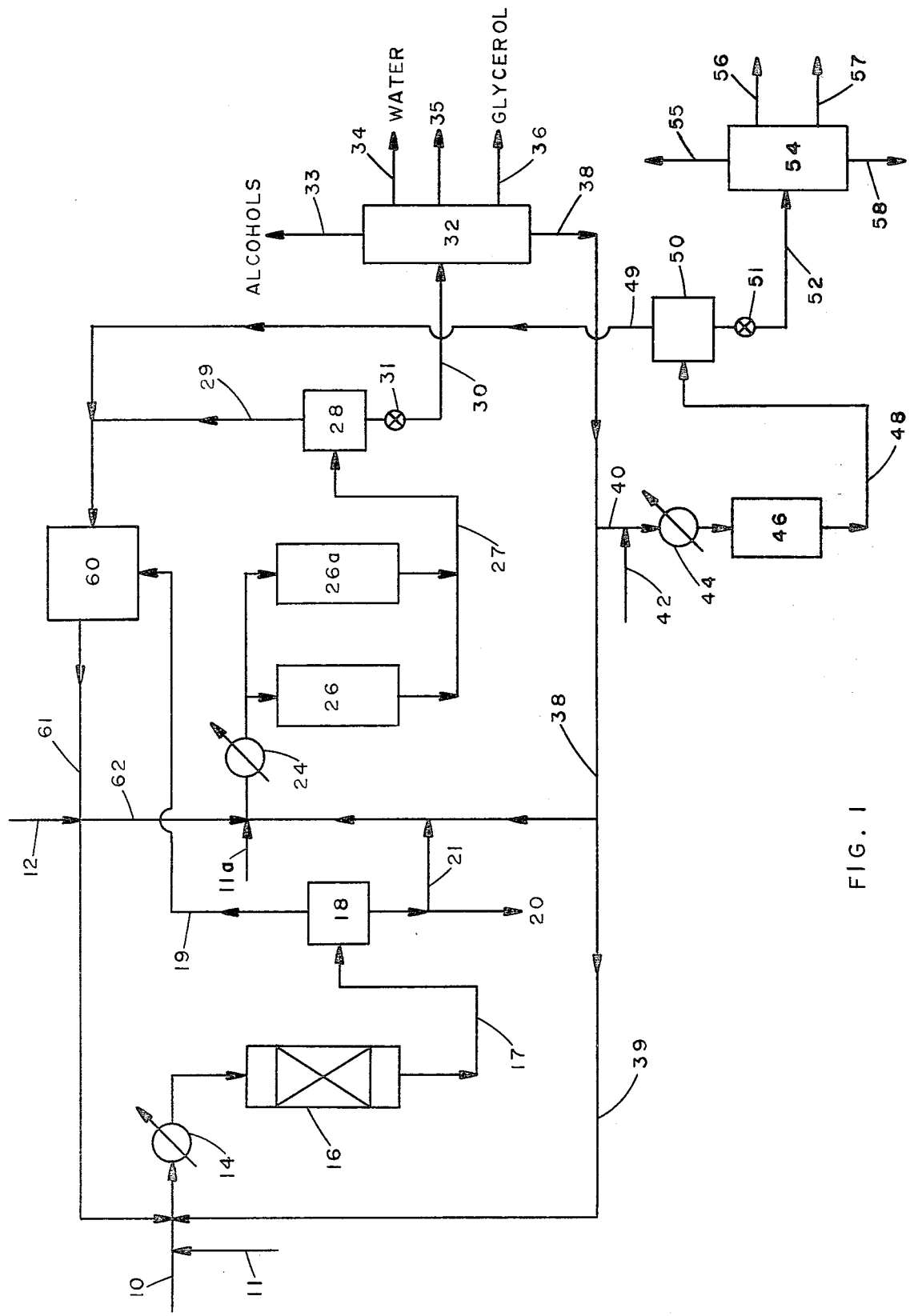
FIG. 1 shows a three-stage catalytic process for hydrogenation of glucose to produce polyols, with recycle of some by-product sugars to the aldose hydrogenation and/or alditol hydrogenolysis steps for further conversion, and the further reaction of heavy material in a third-stage, catalytic reactor.

As shown in the drawing, a glucose-water feed solution at 10 is mixed with an alkaline promotor material at 11 such as calcium hydroxide. The resulting mixture is pressurized and passed with hydrogen from 12 through preheater 14 to fixed-bed catalytic reactor 16 for hydrogenation reaction to produce mainly sorbitol. The promotor material added at 11 should be sufficient to control pH of feedstream to range of 7–14 to prevent leaching damage to the catalyst in reactor 16. The catalyst is preferably a reduced and stabilized nickel on silica-alumina support, and usually contains 50–66 W % nickel. Catalyst particle size of 0.060 to 0.250 inch can be used. The reaction conditions which can be used in reactor 16 are 130°–180° C. temperature, 500–2000 psig hydrogen partial pressure, and 0.5–3.5 Vf/hr/Vc space velocity to achieve at least about 90 W % conversion of the glucose feed to sorbitol solution.

The resulting sorbitol solution is withdrawn from reactor 16 as stream 17 and passed to phase separation step 18, from which overhead vapor stream 19 containing mainly hydrogen is withdrawn and passed to hydrogen purification step 60. If desired, some sorbitol product can be withdrawn from the process at 20. The remaining liquid portion 21 is passed with recycled hydrogen at 62 and fresh hydrogen from 12 to fixed bed reactor 26 containing a catalyst, such as about 50–65 W % nickel supported on silica-alumina support, for hydrogenolysis of the sorbitol. Again, sufficient alkaline promotor material should be added at 11a to control the pH of the feed to a range of 7–14.

Reaction conditions useful in reactor 26 are 420°–500° F. temperature, 1200–2000 psig hydrogen partial pressure, 1.5–3.0 Vf/hr/Vc liquid hourly space velocity for achieving at least about 30 W % conversion of the sorbitol (or other alditol) feed to polyols, principally glycerol and a lesser concentration of glycols, etc. Catalyst age is maintained between about 10 and 200 hours and preferably 15–100 hours by periodic regeneration of the catalyst as necessary to maintain its activity, such as by providing dual reactors 26 and 26a connected in parallel with one reactor being in use while the catalyst in the other reactor is regenerated alternately. The used catalyst is regenerated by first washing with a solvent such as water, and then contacting the catalyst with reducing gas such as hydrogen at a temperature above the reaction temperature; e.g., 500°–650° F. temperature, and at reduced pressure such as atmospheric pressure for 2 to 10 hours duration.

The reaction products from reactor 26 (or 26a) are withdrawn at 27 and passed to a recovery or separation step 28, from which hydrogen-containing gas is removed at 29 and is passed to hydrogen purification step 40. The remaining liquid stream 30 is passed to recovery step 32, which usually comprises one or more distillation columns, with the final column operating at subatmospheric pressure of 10–100 mm. Hg. A vapor stream containing alcohols is removed at 33, water vapor is removed at 34, glycols are withdrawn at 35, and 40–90 W % glycerol product is withdrawn at 36. Unreacted sorbitol is removed at 38 and partly recycled to the hydrogenolysis reaction steps 16 and 26 as desired for further processing as described below. Also, if desired, the heavy withdrawal stream 38 containing $C_4$ and $C_6$ sugars and polyglycerols can be diluted with alcohol such as methanol from 33 and water 34 and recycled back to reactor 16 for further conversion to alditols.

An important alternative to recycling diluted stream 38 to reactor 16, is to pressurize and pass it with hydrogen at 42 through preheater 44 as feed to a third-stage catalytic reactor 46. This reactor is preferably a fixed-bed unit and is usually operated at more severe conditions than reactors 16 and 26, such as 450°–550° F. temperature, 2000–3000 psig hydrogen partial pressure, and space velocity of 0.5–2.0 $V_f/Hr/V_r$. Feedstream 40 usually contains 5–15 W % concentration of aldoses and alditols, with the remainder being glycerols and water. The catalyst used can be the same as in the first-stage reactor 16, and is preferably 50–66 W % nickel on an inert support such as silica-alumina. Virtually total conversion of the remaining sugars and alditols is achieved to produce additional glycerol and glycols. Also, polyglycerols are reacted to extinction in this step.

The reaction products from reactor 46 are withdrawn at 48 and passed to separation step 50. Similarly as for separation step 28, a hydrogen-containing gas stream is withdrawn at 49 and passed to hydrogen purification step 60. The remaining liquid stream 52 is passed to recovery step 54, from which are withdrawn vapor stream 55, alcohols at 56, water at 57, and useful polyols product stream 58 similarly as for recovery step 32.

Although this invention has been described in terms of the accompanying drawing and preferred embodiment, it is recognized that many modifications of the invention can be made without departing from the spirit and scope thereof, which is defined solely by the following claims.

What I claim is:

1. A process for catalytic conversion of monosaccharides to produce polyols, comprising the steps of:

(a) providing a feedstream containing at least about 20 W % monosaccharide solution and having pH of 7 to 14;

(b) preheating the feed and hydrogen gas to at least about 100° C., and passing the heated feedstream mixture through a first stage fixed bed catalytic reaction zone containing a stabilized high activity nickel on silica-alumina support containing 50–60 W % porous nickel and having 0.060–0.250 inch diameter particle size and surface area of 140–180 $M^2$/gm;

(c) maintaining said first reaction zone at conditions of 130°–180° C. temperature, 500–2000 psig partial pressure of hydrogen, and 0.5–3.5 V.Hr/V space velocity, for achieving at least about 90 W % conversion of the feed to alditols;

(d) withdrawing product containing alditol solution and passing it with a promotor material and hydrogen gas to a second-stage fixed-bed reaction zone containing a particulate high activity stabilized metal catalyst which catalyst comprises 50–65 W % porous nickel on an inert support, has 4–12 mesh (0.187–0.66 inch) particle size (U.S. Sieve Series), and a catalyst age of 8–200 hours before regeneration to maintan its activity;

(e) maintaining said second reaction zone conditions within the range of 430°–490° F. temperature, 1200–2000 psig hydrogen partial pressure, and 1.5–3.0 liquid hourly space velocity (LHSV) for achieving at least about 30 W % conversion of the alditol to products;

(f) withdrawing from the second reaction zone a product stream in which the alditol is converted between about 30 to 80 W % to yield glycerol and glycol products, and passing the polyol-containing stream to a recovery step from which mainly glycerol product is withdrawn;

(g) recycling a heavy purge stream containing aldose and alditols diluted with alcohol and/or water to the first stage reaction zone for further conversion to alditols and glycerols, respectively.

2. The process of claim 1, wherein the pH of the feedstream to each reaction zone is controlled within range of 7.5 to 12 by adding sodium hydroxide comprising 0.1 to 2.0 W % of the feedstream to avoid leaching metal from the catalyst.

3. The process of claim 1, wherein the first reaction zone conditions are maintained at 140°–170° C. temperature, 750–1600 psig partial pressure of hydrogen, and 0.6–3.3 V/Hr/V space velocity and hydrogen gas/liquid feed ratio of 1000–5000 at standard conditions.

4. The process of claim 1, wherein the feed to the first stage zone is 30–60 W % glucose in water solution and the glucose conversion therein is 98.5–99.9 W % to sorbitol.

5. The process of claim 1, wherein the feedstream to said first zone is 20–50 W % mannose solution and the product is mannitol solution.

6. The process of claim 1, wherein the feedstream to the second reaction zone contains 20–60 W % sorbitol in aqueous solution, the reaction zone conditions are maintained within the range of 440°–480° F. temperature, 1400–1900 psig hydrogen partial pressure, and 2.0–2.7 liquid hourly space velocity, and catalyst age is 20–200 hours before regeneration, and wherein the sorbitol feed solution is converted about 30–70 W % to yield mainly glycerol product with the remainder being glycols.

7. The process of claim 1, wherein the feedstream to the first stage is 30–60 W % glucose in alcohol solution and feedstream to the second stage reaction zone is 15–50 W % sorbitol in alcohol solution.

8. The process of claim 1, wherein the catalyst in the second stage reaction zone is regenerated following at least about 20 hours use, by washing said catalyst with a solvent and contacting it with hydrogen at 500°–650° F. temperature for at least 2 hours, then returning the catalyst to use.

9. A process for catalytic conversion of monosaccharides to produce polyols, comprising the steps of:

(a) providing a feedstream containing at least about 20 W % monosaccharide solution and having a pH of 7 to 14;

(b) preheating the feed and hydrogen gas to at least about 100° C., and passing the heated feedstream mixture through a first stage fixed bed catalytic reaction zone containing a high activity metal catalyst;

(c) maintaining said first reaction zone at conditions of 130°–180° C. temperature, 500–2000 psig partial pressure of hydrogen, and 0.5–3.5 V/Hr/V space velocity, for achieving at least about 90 W % conversion of the feed to alditols;

(d) withdrawing product containing alditol solution and passing it with a promotor material and hydrogen gas to a second stage fixed bed reaction zone containing a particulate high activity stabilized metal catalyst;

(e) maintaining said second reaction zone conditions within the range of 430°–490° F. temperature, 1200–2000 psig hydrogen partial pressure, and 1.5–3.0 liquid hourly space velocity (LHSV) for achieving at least about 30 W % conversion of the alditol to products;

(f) withdrawing from the second reaction zone a product stream in which the alditol is converted between about 30 and 80 W % to yield glycerol and glycol products, and passing the polyol-containing stream to a recovery step from which mainly glycerol product is withdrawn; and (g) withdrawing from said recovery step a heavy purge stream containing sugars and polyglycols and passing said stream to a third-stage catalytic reaction zone for further conversion to alditols.

10. The process of claim 9, wherein the catalyst used in said third stage reaction zone is 50–60 W % nickel on silica-alumina support, and the reaction zone conditions are maintained within the range of 450°–550° F. temperature, 2000–3000 psig hydrogen partial pressure, and 0.5–2 $V_f$/Hr/$V_r$ space velocity.

* * * * *